United States Patent
Parida et al.

(10) Patent No.: US 11,031,092 B2
(45) Date of Patent: Jun. 8, 2021

(54) TAXONOMIC ANNOTATION OF VARIABLE LENGTH METAGENOMIC PATTERNS

(71) Applicant: INTERNATIONAL BUSINESS MACHINES CORPORATION, Armonk, NY (US)

(72) Inventors: Laxmi Parida, Mohegan Lake, NY (US); Enrico Siragusa, White Plains, NY (US); Filippo Utro, Pleasantville, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 462 days.

(21) Appl. No.: 15/800,583

(22) Filed: Nov. 1, 2017

(65) Prior Publication Data
US 2019/0130063 A1    May 2, 2019

(51) Int. Cl.
*G16B 10/00*    (2019.01)
*G06F 16/28*    (2019.01)
*G06F 16/22*    (2019.01)
*G16B 40/00*    (2019.01)
*G16B 50/10*    (2019.01)

(52) U.S. Cl.
CPC ......... *G16B 10/00* (2019.02); *G06F 16/2246* (2019.01); *G06F 16/285* (2019.01); *G16B 40/00* (2019.02); *G16B 50/10* (2019.02)

(58) Field of Classification Search
CPC ........ G16B 10/00; G16B 40/00; G16B 50/10; G06F 16/285; G06F 16/2246
See application file for complete search history.

(56) References Cited

U.S. PATENT DOCUMENTS 6,571,230 B1    5/2003    Parida
7,203,680 B2    4/2007    Parida
(Continued)

OTHER PUBLICATIONS

Comin et al ("Assembly-free genome comparison based on next-generation sequencing reads and variable length patterns"), Mar. 31, 2014, pp. 1-10 (Year: 2014).*
(Continued)

*Primary Examiner* — Jared M Bibbee
(74) *Attorney, Agent, or Firm* — Tutunjian & Bitetto, P.C.; Kristofer Haggerty

(57) ABSTRACT

A computer-implemented method, computer program product, and computer processing system are provided for metagenomic pattern classification. The method includes pre-processing, by a processor, a taxonomy tree associated with a genome database to extract taxonomy related information therefrom. The genome database includes a plurality of genome sequences. The method further includes building, by the processor, a suffix tree on the genome database. The method also includes annotating, by the processor, nodes in the suffix tree, using a plurality of right maximal patterns derived from the extracted taxonomy related information as annotations, such that each of the plurality of right maximal patterns in the suffix tree points to a respective one of a plurality of nodes in the taxonomy tree and such that a leaf node in the taxonomy tree represents a respective sample organism. The annotations are configured to function as classifications for the plurality of genome sequences.

20 Claims, 8 Drawing Sheets

(56) References Cited

U.S. PATENT DOCUMENTS

| | | | |
|---|---|---|---|
| 7,739,052 B2 | 6/2010 | Parida | |
| 8,423,339 B2 | 4/2013 | Parida et al. | |
| 8,428,882 B2 | 4/2013 | Chiu et al. | |
| 9,275,059 B1* | 3/2016 | Vijendra | G06F 16/10 |
| 9,507,807 B1* | 11/2016 | Florissi | G06F 16/20 |
| 2014/0316716 A1* | 10/2014 | Jiang | G16B 30/00 |
| | | | 702/20 |
| 2014/0371109 A1* | 12/2014 | McMillen | H01L 21/76886 |
| | | | 506/38 |
| 2016/0103956 A1* | 4/2016 | Conway | G16B 30/00 |
| | | | 702/19 |
| 2017/0011168 A1* | 1/2017 | Vockley | G16B 20/00 |
| 2017/0152548 A1 | 6/2017 | Wigler et al. | |
| 2018/0203976 A1* | 7/2018 | Chiu | G16B 20/00 |

OTHER PUBLICATIONS

Abouelhoda, et al., "Enhanced Suffix Arrays and Applications", CRC Press, LLC, 2001, pp. 1-28.

Khan, et al., "A Practical Algorithm for Finding Maximal Exact Matches in Large Sequence Datasets Using Sparse Suffix Arrays", Bioinformatics, Apr. 2009, pp. 1609-1616, vol. 25 No. 13.

Wood at al., "Kraken: Ultrafast Metagenomic Sequence Classification Using Exact Alignments", Genome Biology, Mar. 2014, pp. 1-12.

Zhuang, "Discovery of Flexible Gap Patterns from Sequences", A thesis presented to the University of Waterloo in fulfillment of the thesis requirement for the degree of Doctor of Philosophy in Systems Design Engineering, 2014, pp. 1-129.

\* cited by examiner

|   |     | gsa |     |          |
|---|-----|-----|-----|----------|
| i | tax | id  | pos | $S_{gsa}$ |
| 0 | -   | 1   | 1   | aat      |
| 1 | 4   | 2   | 1   | aat      |
| 2 | -   | 0   | 0   | agtg     |
| 3 | 5   | 1   | 2   | at       |
| 4 | -   | 2   | 2   | at       |
| 5 | 6   | 3   | 1   | at       |
| 6 | -   | 1   | 0   | caat     |
| 7 | 6   | 0   | 3   | g        |
| 8 | -   | 2   | 0   | gaat     |
| 9 | -   | 0   | 1   | gtg      |
| 10 | 6  | 1   | 3   | t        |
| 11 | -  | 2   | 3   | t        |
| 12 | -  | 3   | 2   | t        |
| 13 | -  | 3   | 0   | tat      |
| 14 | -  | 0   | 2   | tg       |

|   |     |    | GBWT($S$) |   | GBWT($\overline{S}$) |   |
|---|-----|----|------|--------|------|--------|
| i | tax | id | gbwt | $S_{gsa}$ | gbwt | $\overline{S}_{gsa}$ |
| 0 | -   | -  | g    | $\$_0$    | a    | $\$_0$    |
| 1 | -   | -  | t    | $\$_1$    | c    | $\$_1$    |
| 2 | -   | -  | t    | $\$_2$    | g    | $\$_2$    |
| 3 | -   | -  | t    | $\$_3$    | t    | $\$_3$    |
| 4 | -   | -  | c    | aat$\$_1$ | g    | a$\$_0$   |
| 5 | 4   | -  | g    | aat$\$_2$ | t    | aac$\$_a$ |
| 6 | -   | 0  | $\$_0$ | agtg$\$_0$ | t | aag$\$_2$ |
| 7 | 5   | -  | a    | at$\$_1$  | a    | ac$\$_1$  |
| 8 | -   | -  | a    | at$\$_2$  | a    | ag$\$_2$  |
| 9 | 6   | -  | t    | at$\$_3$  | t    | at$\$_3$  |
| 10 | -  | 1  | $\$_1$ | caat$\$_1$ | a | c$\$_1$   |
| 11 | 6  | -  | t    | g$\$_0$   | a    | g$\$_2$   |
| 12 | -  | 2  | $\$_2$ | gaat$\$_2$ | t | ga$\$_0$  |
| 13 | -  | 0  | a    | gtg$\$_0$ | $\$_0$ | gtga$\$_0$ |
| 14 | 6  | -  | a    | t$\$_1$   | a    | t$\$_3$   |
| 15 | -  | -  | a    | t$\$_2$   | $\$_1$ | taac$\$_1$ |
| 16 | -  | -  | a    | t$\$_3$   | $\$_2$ | taag$\$_2$ |
| 17 | -  | 3  | $\$_3$ | tat$\$_3$ | $\$_3$ | tat$\$_3$ |
| 18 | -  | 0  | g    | tg$\$_0$  | g    | tga$\$_0$ |

FIG. 8

TAXONOMIC ANNOTATION OF VARIABLE LENGTH METAGENOMIC PATTERNS

BACKGROUND

Technical Field

The present invention relates generally to genomes and, in particular, to taxonomic annotation of variable length metagenomic patterns.

Description of the Related Art

Genome databases are growing everyday with hundreds of thousands of organisms. Hence, it can be an onerous task to trawl through the database. Accordingly, there is a need for a way to efficiently annotate metagenome databases for pattern classification purposes.

SUMMARY

According to an aspect of the present invention, a computer-implemented method is provided for metagenomic pattern classification. The method includes pre-processing, by a processor, a taxonomy tree associated with a genome database to extract taxonomy related information therefrom. The genome database includes a plurality of genome sequences. The method further includes building, by the processor, a suffix tree on the genome database. The method also includes annotating, by the processor, nodes in the suffix tree, using a plurality of right maximal patterns derived from the extracted taxonomy related information as annotations, such that each of the plurality of right maximal patterns in the suffix tree points to a respective one of a plurality of nodes in the taxonomy tree and such that a leaf node in the taxonomy tree represents a respective sample organism. The annotations are configured to function as classifications for the plurality of genome sequences.

According to another aspect of the present invention, a computer program product is provided for metagenomics pattern classification. The computer program product includes a non-transitory computer readable storage medium having program instructions embodied therewith. The program instructions are executable by a computer to cause the computer to perform a method. The method includes pre-processing, by a processor, a taxonomy tree associated with a genome database to extract taxonomy related information therefrom. The genome database includes a plurality of genome sequences. The method further includes building, by the processor, a suffix tree on the genome database. The method also includes annotating, by the processor, nodes in the suffix tree, using a plurality of right maximal patterns annotated from the extracted taxonomy related information, such that each of the plurality of right maximal patterns in the suffix tree points to a respective one of a plurality of nodes in the taxonomy tree and such that a leaf node in the taxonomy tree represents a respective sample organism. The annotations are configured to function as classifications for the plurality of genome sequences.

According to yet another aspect of the present invention, a computer processing system is provided for classification of genomic patterns. The system includes a processor. The processor is configured to pre-process a taxonomy tree associated with a genome database to extract taxonomy related information therefrom. The genome database includes a plurality of genome sequences. The processor is further configured to build a suffix tree on the genome database. The processor is also configured to annotate nodes in the suffix tree, using a plurality of right maximal patterns derived from the extracted taxonomy related information as annotations, such that each of the plurality of right maximal patterns in the suffix tree points to a respective one of a plurality of nodes in the taxonomy tree and such that a leaf node in the taxonomy tree represents a respective sample organism. The annotations are configured to function as classifications for the plurality of genome sequences.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 7 shows an exemplary generalized suffix array, in accordance with an embodiment of the present invention; and FIG. 8 shows an exemplary generalized bidirectional Burrows-Wheeler Transform (BWT), in accordance with an embodiment of the present invention.

DETAILED DESCRIPTION

The present invention is directed to taxonomic annotation of variable length patterns in a metagenomic database. For the purpose of the invention, the terms "metagenomics(s)", "metatranscriptomic(s)", "genomic(s)" can interchangeably refer to the following: a set of sequences annotated by taxonomic information.

In an embodiment, the present invention can be used to annotate a pattern (of unknown origin) on a taxonomy, given the pattern (of unknown origin) and a reference database of sequences organized in a taxonomic tree.

In an embodiment, right maximal patterns are annotated, as opposed to k-mers. The use of right maximal patterns allows for the classification of patterns of any length as opposed to patterns having a fixed length k.

In an embodiment, the present invention can provide a lossless representation of taxonomic annotated sequences in an efficient amount of space that allows a time efficient pattern classification. In this way, data (sequence) identification, access, and classification times can be reduced, as well as the corresponding computing resources (e.g., processing, memory, bandwidth, etc.) implicated to search a genome database.

It is to be appreciated that the present invention can be used for a myriad of applications. For example, exemplary applications to which the present invention can be applied include, but are not limited to, any of the following: human microbiomes; related to human health; food safety; soil; microbiomes; and so forth. It is to be appreciated that the preceding applications to which the present invention can be applied are merely illustrative and, thus, the present invention can be used for other applications, as readily appreciated by one of ordinary skill in the art given the teachings of the present invention provided herein, while maintaining the spirit of the present invention.

Figure 1:
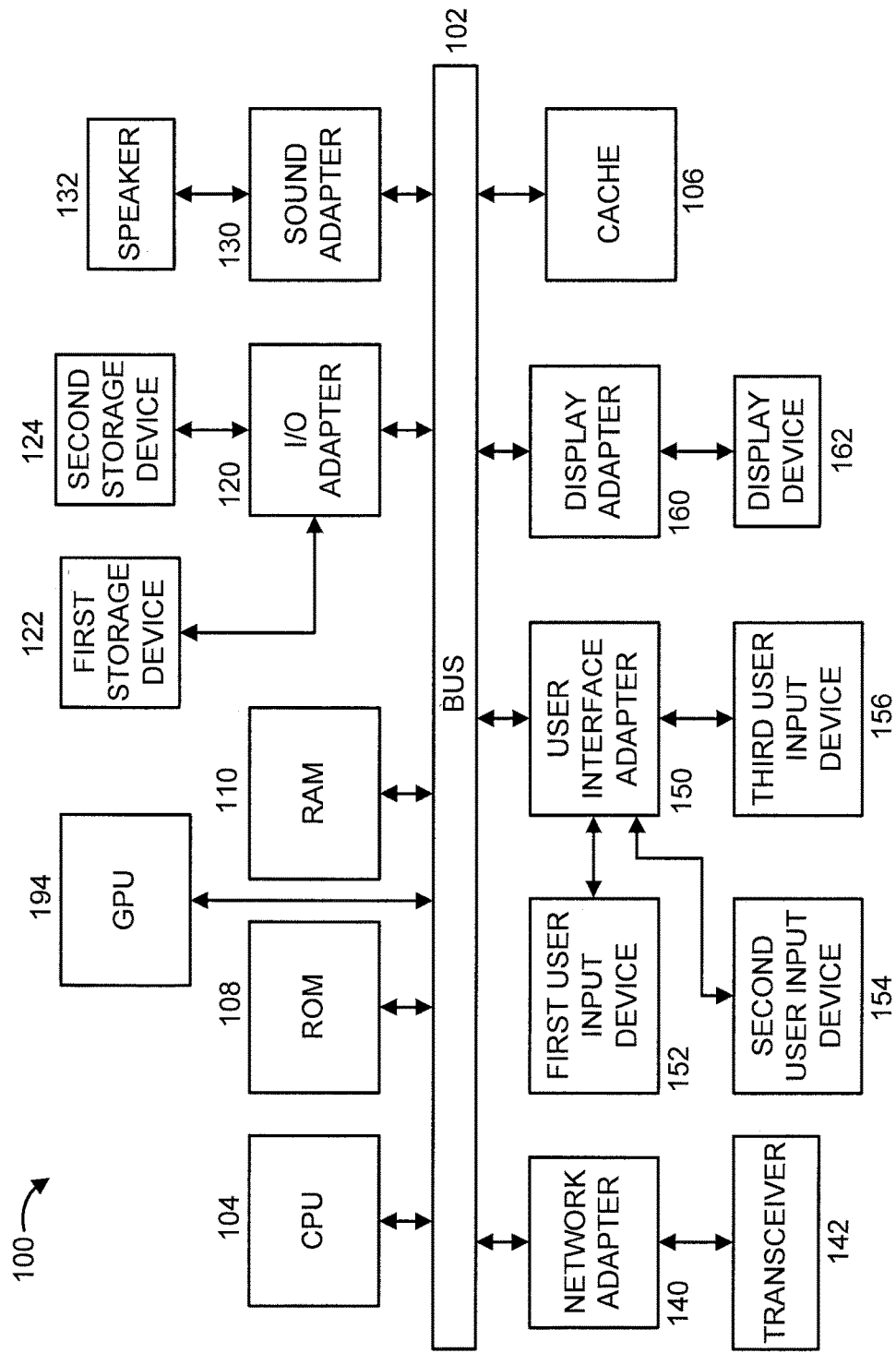
FIG. 1 shows an exemplary processing system to which the present invention may be applied, in accordance with an embodiment of the present invention.

FIG. 1 shows an exemplary processing system 100 to which the invention principles may be applied, in accordance with an embodiment of the present invention. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102. At least one Graphics Processing Unit (GPU) 194 is operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present invention provided herein.

Figure 2:
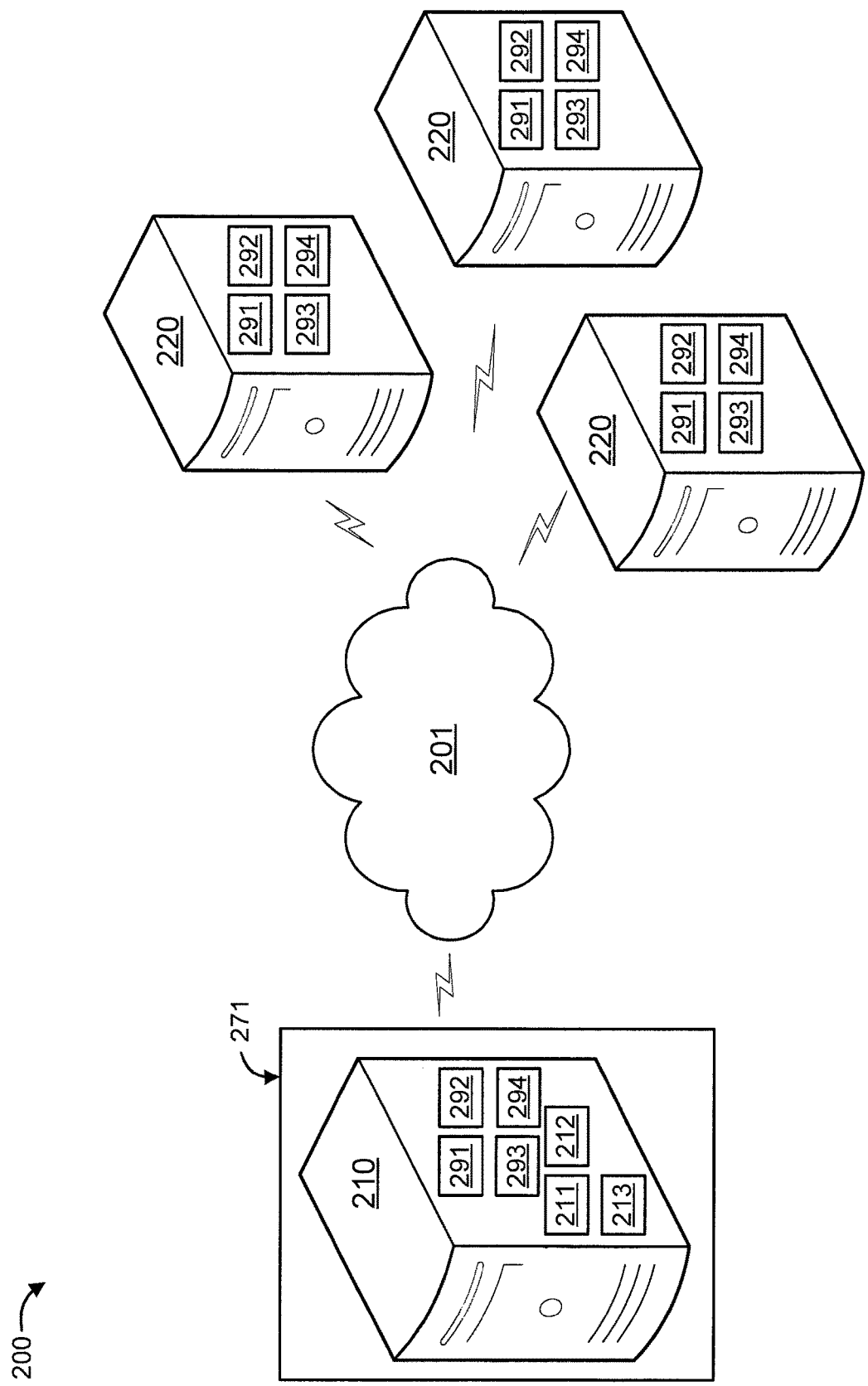
FIG. 2 shows an exemplary system to which the present invention can be applied, in accordance with an embodiment of the present invention.

Moreover, it is to be appreciated that system 200 described below with respect to FIG. 2 is a system for implementing respective embodiments of the present invention. Part or all of processing system 100 may be implemented in one or more of the elements of system 200.

Figure 3:
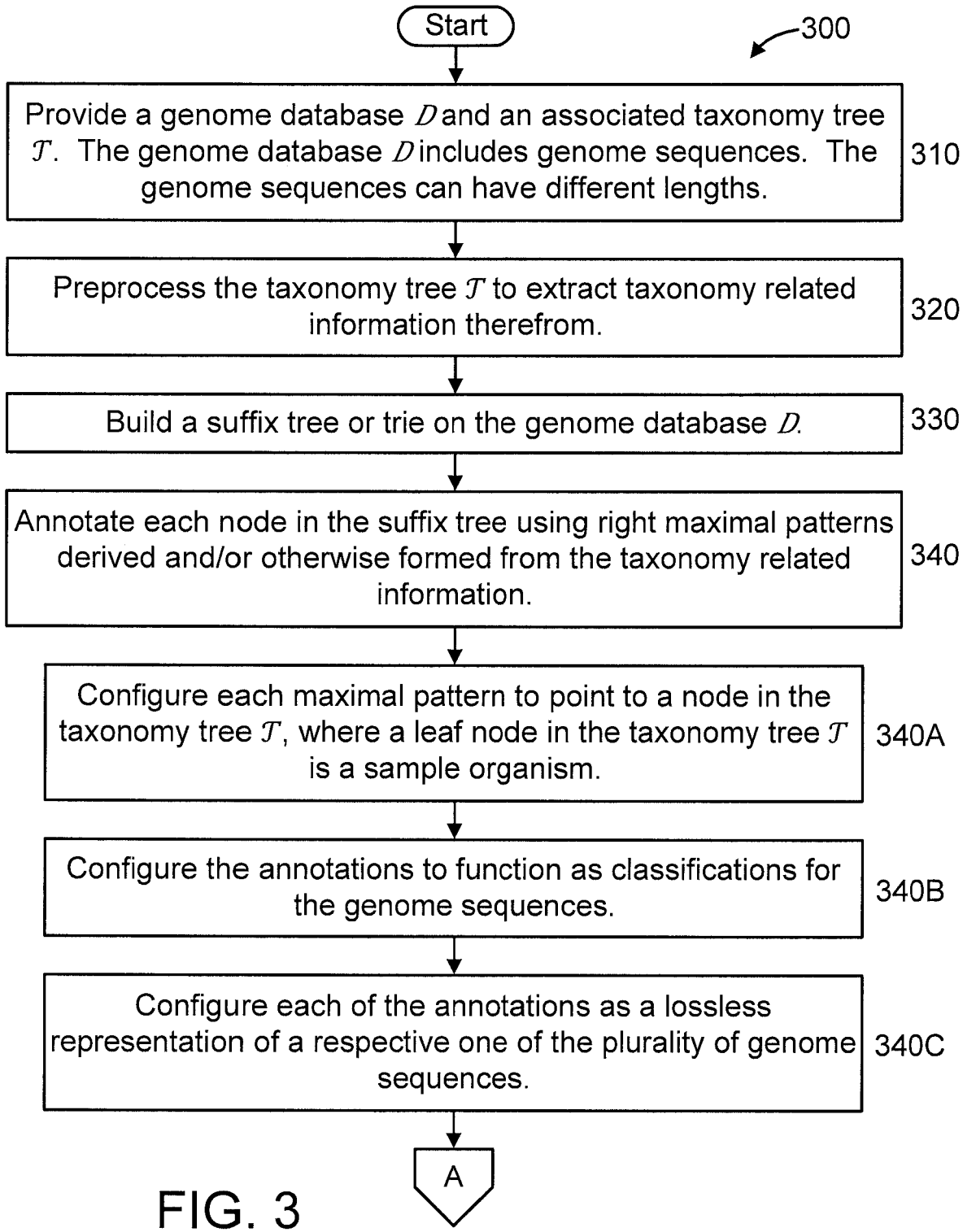
FIGS. 3-4 show an exemplary method for indexing genome databases with taxonomy using variable length patterns, in accordance with an embodiment of the present invention.
Figure 4:
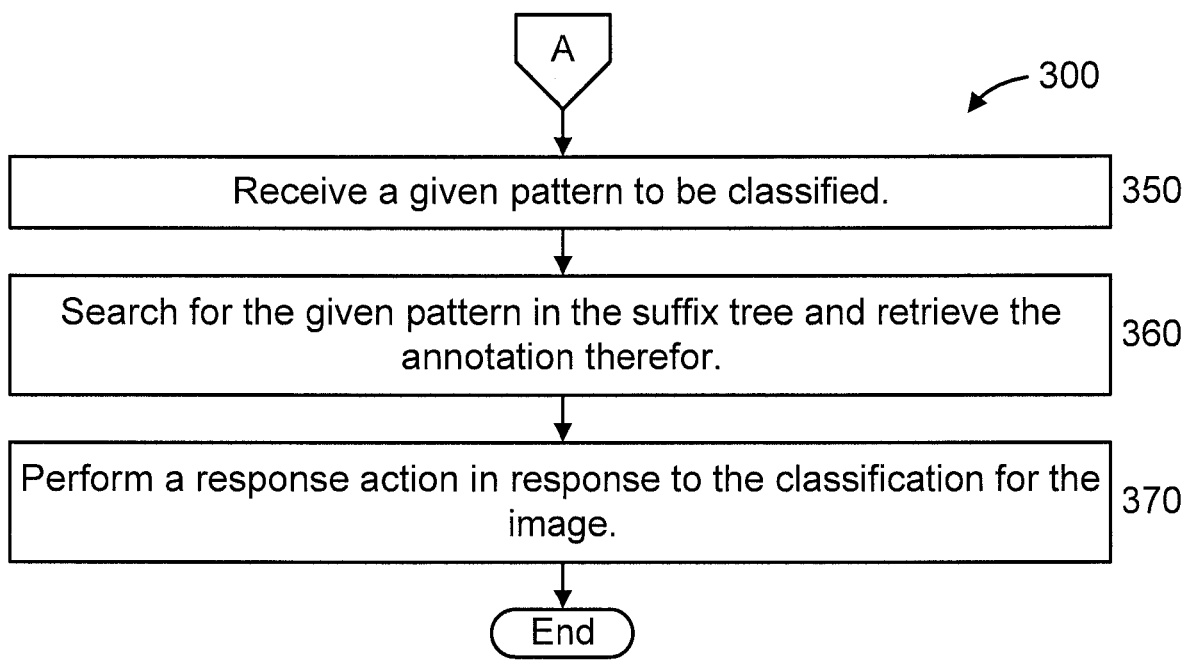

Further, it is to be appreciated that processing system 100 may perform at least part of the method described herein including, for example, at least part of method 300 of FIGS. 3-4. Similarly, part or all of system 200 may be used to perform at least part of method 300 of FIGS. 3-4.

FIG. 2 shows an exemplary system 200 to which the present invention can be applied, in accordance with an embodiment of the present invention. The system 200 includes a computer processing system 210 (e.g., computer processing system 100) and a set of other computer processing systems 220. In an embodiment, one or more of the computer processing systems 210 and 220 can be configured as servers.

The computer processing system 210 includes a genome database D211 and an associated taxonomy tree $\mathcal{T}$ 212. The computer processing system 210 can be configured to perform pre-processing on the genome database D 211 and the associated taxonomy tree $\mathcal{T}$ 212. The pre-processing can involve building and annotating a suffix tree 213 for use in searching the genome database D 211 for an input pattern to be classified/correlated. The computer processing system 210 can be configured to receive patterns to be classified from any of the other computer processing systems 220, classify such patterns using the suffix tree 213, and send a classification therefor to the other computer processing systems 220. The classifications are in the form of space efficient annotations as described in further detail herein below.

The computer processing system 210 further includes at least a processor 291, a memory 292, and a transceiver 293. Moreover, the other computer processing systems 220 at least include a processor 291, a memory 292, a transceiver 293, and a database 294. The processor 291 and memory 292 of the computer processing system 210 can be configured to perform indexing of the genome database D 211 with taxonomy $\mathcal{T}$ 212 using maximal patterns. The processor 291 and the memory 292 of the other computer processing systems can be configured to provide patterns to be classified. The transceivers 293 in any of the systems 210 and 220 can be configured to send and receive patterns. The databases 294 of the other computer processing systems 220 can store patterns to be classified as well as classifications for patterns already classified.

In the embodiment shown in FIG. 2, the elements thereof are interconnected by a network(s) 201. However, in other embodiments, other types of connections can also be used. Moreover, in an embodiment, at least one of the elements of system 200 is processor-based (in the shown example, all are processor-based). Further, while one or more elements may be shown as separate elements, in other embodiments, these elements can be combined as one element. The converse is also applicable, where while one or more elements may be part of another element, in other embodiments, the one or more elements may be implemented as standalone elements. Moreover, one or more elements of FIG. 2 can be implemented in a cloud configuration including, for example, in a distributed configuration. Additionally, one or more elements in FIG. 2 may be implemented by a variety of devices, which include but are not limited to, Digital Signal Processing (DSP) circuits, programmable processors, Application Specific Integrated Circuits (ASICs), Field Programmable Gate Arrays (FPGAs), Complex Programmable Logic Devices (CPLDs), and so forth. These and other variations of the elements of system 200 are readily determined by one of ordinary skill in the art, given the teachings of the present invention provided herein, while maintaining the spirit of the present invention.

FIGS. 3-4 show an exemplary method 300 for indexing genome databases with taxonomy using variable length patterns (right maximal patterns), in accordance with an embodiment of the present invention. In an embodiment, steps 310-340 of method 300 can be considered to correspond to a pre-processing phase or stage, while steps 350-360 can be considered to correspond to a classification phase or stage.

At step 310, provide a genome database D and an associated taxonomy tree T. The genome database D includes genome sequences. The genome sequences can have different lengths.

At step 320, preprocess the taxonomy tree $\mathcal{T}$ to extract taxonomy related information therefrom. The taxonomy related information can include, but is not limited to, any of the following: Lowest Common Ancestor (LCA) queries; and any function of the right maximal pattern and the LCA. The taxonomy related information is extracted at step 320 for later use (at step 340).

At step 330, build a suffix tree or trie on the genome database D. The suffix tree can be built using, for example, any of the following: (1) a (bi-directional) FM-index; (2) an (enhanced) suffix array; and (3) a (compressed) suffix tree. The preceding structures are merely illustrative and, thus, other structures can also be used to build the suffix tree, while maintaining the spirit of the present invention.

At step 340, annotate each node in the suffix tree using right maximal patterns derived and/or otherwise formed from the taxonomy related information (extracted at step 320). The resultant annotated suffix tree provides a medium upon which to perform quick searches in order to obtain classifications for input sequences to be searched. Hence, the proposed invention improves the functionality of the genome database D as well as the computer processing system that includes the genome database D.

In an embodiment, step 340 includes one or more of steps 340A-C.

At step 340A, configure each maximal pattern to point to a node in the taxonomy tree $\mathcal{T}$, where a leaf node in the taxonomy tree $\mathcal{T}$ is a sample organism.

At step 340B, configure the annotations to function as classifications for the genome sequences.

At step 340C, configure each of the annotations as a lossless representation of a respective one of the plurality of genome sequences.

At step 350, receive a given pattern to be classified. The given pattern can be, but is not limited to, a read (pattern) from Next Generation Sequencing (NGS) data and so forth.

At step 360, search for the given pattern in the suffix tree and retrieve the annotation therefor. In an embodiment, as noted above, the annotation includes and/or otherwise represents a classification of the given pattern.

At step 370, perform an action responsive to the annotation/classification of the given pattern. The action can include, but is not limited to, any of the following: sequence alignment (e.g., using one or more ASICs or other specially programmed computing devices); microbiome based tasks (e.g., binning and/or profiling); metatranscripts abundance estimation; and so forth.

Herein, a method is described for annotating generalized suffix arrays and BWTs in order to answer lowest taxonomic unit (LTU) queries in constant time for patterns of arbitrary length. The annotation method is not confined to the specific application of LTUs and can be used for general-purpose annotation, as readily appreciated by one of ordinary skill in the art, given the teachings of the present invention provided herein.

Figure 5:
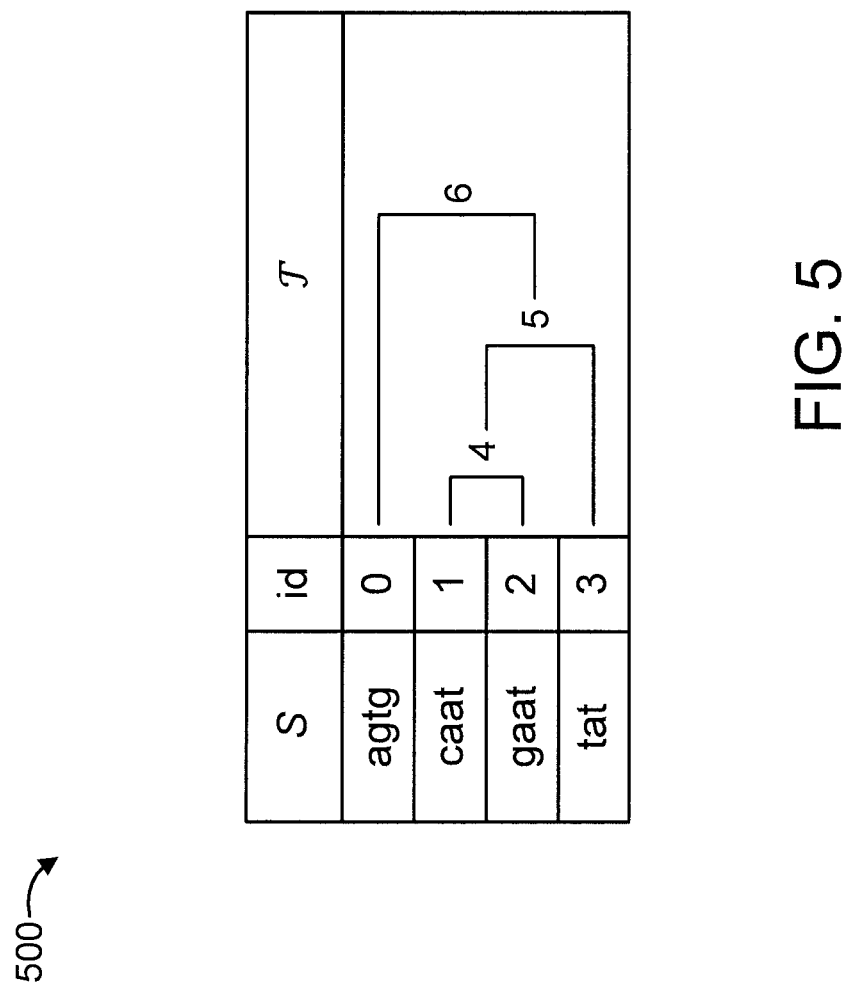
FIG. 5 shows an exemplary taxonomic database to which the present invention can be applied, in accordance with an embodiment of the present invention.

FIG. 5 shows an exemplary taxonomic database 500 to which the present invention can be applied, in accordance with an embodiment of the present invention.

The taxonomic database (S, $\mathcal{T}$) 500 includes a collection of strings S={$s_0, s_1, \ldots, s_{m-1}$} of total length n over the ordered alphabet $\Sigma$={a, c, g, t} and a taxonomic tree $\mathcal{T}$, i.e., a rooted tree with m leaves labeled by the indexes of strings in S and internal nodes referring to taxonomic units. The taxonomic database 500 further includes an id for each of the strings. Given a pattern string p over $\Sigma$, the problem is to retrieve the lowest taxonomic unit (LTU) in $\mathcal{T}$ where p occurs. The taxonomic database (S, $\mathcal{T}$) is given in advance and can be preprocessed.

The LTU between 1 and 3 is 5. The LTU between 0 and 4 is 6.

Figure 6:
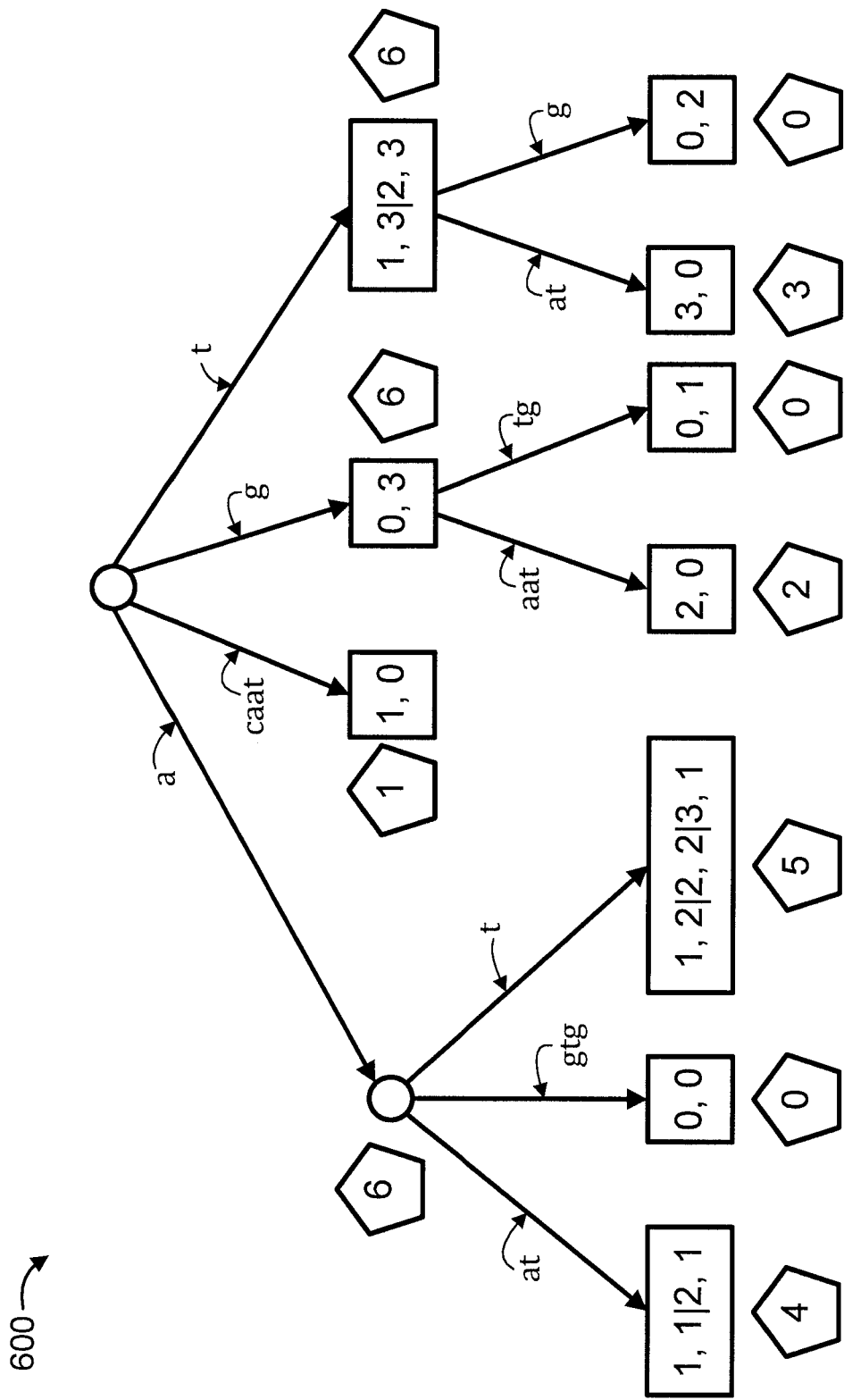
FIG. 6 shows an exemplary generalized suffix tree, in accordance with an embodiment of the present invention.

FIGS. 6-8 hereinafter show examples based on taxonomic database 500 for illustrative purposes.

Initially, we conceptualize taxonomic annotation on generalized suffix trees (GSTs) and thereafter show how to annotate generalized suffix arrays and bidirectional BWTs.

A description will now be given of a generalized suffix tree, in accordance with an embodiment of the present invention.

The description will be provided with respect to FIG. 6, which shows an exemplary generalized suffix tree 600, in accordance with an embodiment of the present invention. For illustrative purposes, the generalized suffix tree 600 of strings S is annotated for LTU queries on taxonomic tree $\mathcal{T}$. The involved database is database (S, $\mathcal{T}$) shown in FIG. 5. In FIG. 6, non-terminal nodes are depicted as circles, terminal nodes are depicted as squares, and LTU annotations are depicted inside pentagons. The LTU of pattern "a" is 6 while the LTU of pattern "aa" is 4.

A practical definition of generalized suffix tree is adopted that is based on terminal nodes in addition to leaves and branching internal nodes. The definition allows the present invention to work on arbitrary collections of strings without introducing sentinel characters, e.g., $. In what follows, we denote the l-th suffix of string $s_k$ as $S_{(k,l)}$:=$s_k[l] \ldots s_k[|s_k|-1]$ where $|s_k|$ is the length of string $s_k$.

The generalized suffix tree of S, abbreviated as GST(S), is a lexicographically ordered tree data structure having one node designated as the root. Each node v of GST(S) provides the following operations:

CLD(v) returns the nodes children of v;
SUF(v) returns a list of pairs s.t. pair (k, l) refers to suffix $S_{(k,l)}$;
LABEL(v) returns a string over $\Sigma$ or the empty string if v is the root;
REPR(v) returns REBR(u)·LABEL(v) where u is the parent of v.

We say that:
Node v is a leaf if |CLD(v)|=0 and internal otherwise; and
Node v is terminal if |SUF(v)|≥1 and non-terminal otherwise.

The GST(S) has the following properties:
For each (k, l) in SUF(v), REPR(v) spells exactly $S_{(k,l)}$;
Each leaf is terminal; and
Each non-terminal node v is branching, i.e., |CLD(v)|≥2, and LABEL(w) for all w∈CLD(v) begin with distinct characters.

As each suffix in S is associated with one terminal node, GST(S) has at most n terminal nodes. Furthermore, because of the branching property, GST(S) has at most n−1 non-terminal nodes. Therefore, we have to annotate at most 2n−1 nodes.

We now describe the annotation of GST(S) to answer LTU queries in constant time given node v. We denote the lowest common ancestor (LCA) of nodes u and v in $\mathcal{T}$ by $LCA_{\mathcal{T}}(u, v)$ and the iterated LCA as follows:

$$LCA_{\mathcal{T}}(u,\ldots,y,z)=LCA_{\mathcal{T}}(u,LCA_{\mathcal{T}}(\ldots,LCA_{\mathcal{T}}(y,z))) \quad (1)$$

We define $IDS(v)=\{k:(k, l)\in SUF(v)\}$. The LTU of node v with $CLD(v)=\{w_0, w_1, \ldots, w_{k-1}\}$ is as follows:

$$LTU_{\mathcal{T}}(v)=LCA_{\mathcal{T}}(IDS(v), LTU_{\mathcal{T}}(w_0), LTU_{\mathcal{T}}(w_1), \ldots, LTU_{\mathcal{T}}(w_{k-1})) \quad (2)$$

Before annotating GST(S), we preprocess $\mathcal{T}$ to answer LCA queries in constant time. In practice, we reduce LCA queries to range minimum queries (RMQ). Subsequently, we compute $LTU_{\mathcal{T}}$ (for all nodes of GST(S) in a single post-order traversal. The annotation of GST(S) thus takes $\mathcal{O}(n)$ time.

A description will be given regarding a generalized suffix array, in accordance with an embodiment of the present invention.

The description will be provided with respect to FIG. 7, which shows an exemplary generalized suffix array 700, in accordance with an embodiment of the present invention. For illustrative purposes, the generalized suffix array 700 of strings S is annotated for LTU queries on taxonomic tree $\mathcal{T}$. The involved database is database (S, $\mathcal{T}$) shown in FIG. 5. Pattern "agtg" corresponds to a singleton with interval [2, 3) and its LTU is id[2]=0. Pattern "a" corresponds to a leftmost node with interval [0, 6) and its LTU is tax[5]=6. Pattern "at" is not on a singleton nor on a leftmost node, its interval is [3, 6) and its LTU is tax[3]=5.

The generalized suffix array (GSA) of strings S is a pair (id, pas):=gsa of tables of length n where id[i]=k, pos[i]=l and gsa[i]=(k, l). Table gsa represents a permutation of all pairs (k, l) referring to suffixes $S_{(k,l)}$ in S. Pairs in gsa are ordered s.t. $S_{gsa[i-1]} <_{lex} S_{gsa[i]}$ for all $i \in [1; n)$.

Table gsa corresponds to the pre-order concatenation of SUF(v) for all terminal nodes v in GST(S). Each node v of GST(S) is univocally identified by a half-open interval [LB(v), RB(v)) on table gsa and it can be determined by binary searching REPR(v) on gsa. GST(S) corresponds to a recursive partitioning of gsa: the root node corresponds to interval [0, n); if v is an internal node with $CLD(v)=\{w_0, w_1, \ldots, w_{k-1}\}$ then its children intervals are as follows:

$$[LB(v)|SUF(v)|;\, RB(w_0)),\, [RB(w_0);\, RB(w_1)),\, \ldots,\, [RB(w_{k-1});\, RB(v)).$$

GSA(S) can be traversed in linear-time, bottom-up using the additional lcp table and top-down using lcp and child tables. If top-down traversal is bounded to relatively short patterns, a binary search on table gsa is a practical alternative. Similarly, GSA(S) supports pattern search in time $\mathcal{O}(|p| \log n)$ using only table gsa, $\mathcal{O}(|p|+\log n)$ using table lcp and $\mathcal{O}(|p|)$ using lcp and child tables.

We now describe our method to store and retrieve LTUs in constant time once we reach a node v. Traversal on GST(S) to compute LTUs is readily translated onto GSA(S). The problem is how to store and retrieve annotations in GSA(S). We say that leaf v is singleton if LB(v)=RB(v)−1. Furthermore, we say that a node v with parent u is leftmost if LB(u)=RB(v); we determine this condition in constant time by remembering the parent u of v while traversing GSA(S) top-down. Note that we define the root not to be leftmost. We introduce a table tax of size n to store the annotations of all non-singleton nodes. We annotate the LTU of node v as follows:

$$LTU_{\mathcal{T}}(v) = \begin{cases} id[LB(v)] & \text{if } v \text{ is singleton,} \\ tax[RB(v)-1] & \text{if } v \text{ is leftmost,} \\ tax[LB(v)] & \text{otherwise.} \end{cases} \quad (3)$$

If v is singleton, its LTU is already annotated in table id at position LB(v). We show by induction on GST(S) that each non-singleton node v is annotated at an available slot in tax. Prior to annotation both tax[LB(v)] and tax[RB(v)−1] are available; after annotation one of these two slots remains available.

1. If v is a leaf. All slots in tax within interval [LB(v), RB(v)) are available and LB(v)<RB(v)−1 as v is non-singleton. Hence, if v is leftmost tax[LB(v)] remains available, otherwise tax[RB(v)−1] remains available.

2. If v is an internal node with children $CLD(v)=\{w_0, w_1, \ldots, w_{k-1}\}$. Node $w_{k-1}$ is not leftmost and $tax[RB(w_{k-1})-1]$ is supposed to be available by induction. As $RB(w_{k-1})=RB(v)$ then tax[RB(v)−1] is available.

(a) If v is non-terminal. We have |SUF(v)|=0, $LB(w_0)$=LB(v) and $w_0$ is leftmost. By induction $tax[LB(w_0)]$ that is tax[LB(v)] is supposed to be available.

(b) If v is terminal. All slots in tax within interval [LB(v); LB(v)+SUF(v)) are available and SUF(v)≥1, so tax[LB(v)] is available.

After annotation, if v is leftmost tax[LB(v)] remains available, otherwise tax[RB(v)−1] remains available.

A description will now be given regarding a generalized Burrows-Wheeler Transform (GBWT) to which the present invention can be applied, in accordance with an embodiment of the present invention.

The description will be provided with respect to FIG. 8, which shows an exemplary generalized bidirectional Burrows-Wheeler Transform 800, in accordance with an embodiment of the present invention. For illustrative purposes, the generalized bidirectional BWT 800 of strings S is annotated for LTU queries on taxonomic tree $\mathcal{T}$. The involved database is database (S, $\mathcal{T}$) shown in FIG. 5.

Hereinafter, we denote by $\bar{s}=s[|s|-1] \ldots s[1]s[0]$ the reversed string s and by $\bar{S}$ the collection S with all strings reversed. We consider the ordered alphabet $\Sigma_{\$}=\{\$_1, \ldots, \$_m\} \cup \Sigma$ and append $\$_i$ to each string $s_i \in S$. This is to insure that S is primitive, i.e., that no string in S is a power of some other string.

The GBWT of strings S is a table gbwt of length n with:

$$gbwt[i] = \begin{cases} s_{id[i]}[pos[i]-1] & \text{if } pos[i] > 0, \\ \$_{id[i]} & \text{otherwise.} \end{cases} \quad (4)$$

Function RANK(c, i) counts the number of occurrences of character $c \in \Sigma_{\$}$ in the half-open interval [0, i) of gbwt and LF as:

$$LF(c,i)=\Sigma_{a<c}RANK(a,n)+RANK(c,i) \quad (5)$$

Similarly to GSA(S), each node v of GST(S) is univocally identified on GBWT(S) by a half-open interval [LB(v), RB(v)). This interval is now determined by searching REPR(v) backwards on gbwt using LF. For any two nodes u, v of GBWT(S) with REPR(v)=c REPR(u) and $c \in \Sigma$, it holds:

$$LB(v)=LF(c,LB(u)+m)-m \quad (6)$$

$$RB(v)=LF(c,RB(u)+m)-m \quad (7)$$

We adjust the boundaries by m since we have introduced m characters $ in S. Function LF is answered in $\mathcal{O}(1)$ time using o(n|Σ||log|Σ|) extra bits on top of gbwt. Pattern p is searched backwards in $\mathcal{O}(|p|)$ time.

The bidirectional GBWT includes GBWT(S) and GBWT($\overline{S}$) and allows searching simultaneously a pattern p backwards on GBWT(S) and its reverse $\overline{p}$ on GBWT($\overline{S}$). Function LT counts the number of characters lexicographically smaller than $c \in \Sigma_S$ in gbwt within interval [i; j):

$$LT(c,i,j) = \Sigma_{a<c} RANK(a,j) - \Sigma_{a<c} RANK(a,i) \quad (8)$$

If u is a node on GBWT(S), $\overline{u}$ is its corresponding node on GBWT($\overline{S}$) s.t. REPR(u)=$\overline{REPR(\overline{u})}$. Furthermore, if v is with REPR(v)=c REPR(u), the interval of node $\overline{v}$ with REPR($\overline{v}$)=c REPR($\overline{u}$) is determined as follows:

$$LB(\overline{v}) = LB(\overline{u}) + LT(c, LB(u)+m, RB(u)+m) \quad (9)$$

$$RB(\overline{v}) = LB(\overline{v}) + RB(v) - LB(v) \quad (10)$$

We construct an unidirectional BWT to answer LTU queries using only table gbwt of GBWT($\overline{S}$) plus tables id and tax of GBWT(S). If we search pattern $\overline{p}$ backwards on GBWT($\overline{S}$) and arrive on a node $\overline{v}$ with REPR($\overline{v}$)=$\overline{p}$, then node v corresponds to the node reached by searching p backwards on GBWT(S) or forward on GSA(S). Therefore we can still access the annotation at node v using Equation 3. To fill tables id and tax, we traverse top-down GBWT($\overline{S}$) backwards and annotate nodes on GBWT(S) forward. Top-down traversal is feasible in practice if it is bounded to relatively short patterns.

We remark that table id can be obtained as a byproduct of certain BWT construction algorithms instead of slicing table gsa. Furthermore, tables id and tax can be sparsified when the annotation is bounded to relatively short patterns. These and other variations are readily determined by one of ordinary skill in the art, given the teachings of the present invention provided herein, while maintaining the spirit of the present invention.

It is to be appreciated that various can be imposed on the preceding data structures or other data structures can be used, given the teachings of the present invention provided herein, while maintaining the spirit of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A computer-implemented method for metagenomic pattern classification, comprising:
   pre-processing, by a processor, a taxonomy tree built to be associated with a genome database to extract taxonomy related information therefrom from which a plurality of right maximal patterns are derived, the genome database comprising a plurality of genome sequences each of which being read without a fixed length requirement during a-preprocessing of the taxonomy tree;
   wherein the pre-processing further comprises:
   building, by the processor, a suffix tree on the genome database; and
   annotating, by the processor, nodes in the suffix tree, using the plurality of right maximal patterns as annotations, such that each of the plurality of right maximal patterns in the suffix tree points to a respective one of a plurality of nodes in the taxonomy tree and such that a leaf node in the taxonomy tree represents a respective sample organism, the annotations configured to function as classifications for the plurality of genome sequences, wherein the suffix tree is built and the nodes in the suffix tree are annotated as part of a pre-processing of the taxonomy tree.

2. The computer-implemented method of claim 1, further comprising searching, by the processor, for a given pattern in the suffix tree and retrieving an annotation therefor as a classification for the given pattern.

3. The computer-implemented method of claim 2, further comprising performing, by a hardware device, an action responsive to the classification for the given pattern, wherein the hardware device is selected for use on the given pattern based on the classification for the given pattern.

4. The computer-implemented method of claim 1, wherein the suffix tree is a suffix trie not explicitly representing the nodes.

5. The computer-implemented method of claim 1, wherein the suffix tree is a suffix tree explicitly representing the nodes.

6. The computer-implemented method of claim 1, wherein the suffix tree is built using a bi-directional FM-index.

7. The computer-implemented method of claim 1, wherein the suffix tree is built using a suffix array.

8. The computer-implemented method of claim 1, wherein the suffix tree is built using a Burrows-Wheeler Transform.

9. The computer-implemented method of claim 1, wherein the taxonomy related information comprises Lowest Common Ancestor queries.

10. The computer-implemented method of claim 1, wherein the taxonomy related information comprises any function of a given right maximal pattern in the suffix tree and a Lowest Common Ancestor.

11. The computer-implemented method of claim 1, wherein at least some of the genome sequences have different lengths with respect to each other.

12. The computer-implemented method of claim 1, wherein the given sequence comprises a read of Next Generation Sequence data.

13. The computer-implemented method of claim 1, wherein the suffix tree is built to operate without use of a child table.

14. The computer-implemented method of claim 1, wherein each of the annotations is configured as a lossless representation of a respective one of the plurality of genome sequences.

15. The computer-implemented method of claim 1, wherein the suffix tree is built to annotate self-links between any two nodes in the suffix tree without use of a child table.

16. A computer program product for metagenomics pattern classification, the computer program product comprising a non-transitory computer readable storage medium having program instructions embodied therewith, the program instructions executable by a computer to cause the computer to perform a method comprising:
   pre-processing, by a processor, a taxonomy tree built to be associated with a genome database to extract taxonomy related information therefrom from which a plurality of right maximal patterns are derived, the genome database comprising a plurality of genome sequences each of which being read without a fixed length requirement during a-preprocessing of the taxonomy tree;
   wherein the pre-processing further comprises:
   building, by the processor, a suffix tree on the genome database; and
   annotating, by the processor, nodes in the suffix tree, using the plurality of right maximal patterns, such that each of the plurality of right maximal patterns in the suffix tree points to a respective one of a plurality of nodes in the taxonomy tree and such that a leaf node in the taxonomy tree represents a respective sample organism, the annotations configured to function as classifications for the plurality of genome sequences, wherein the suffix tree is built and the nodes in the suffix tree are annotated as part of a pre-processing of the taxonomy tree.

17. The computer program product of claim 16, further comprising searching, by the processor, for a given pattern in the suffix tree and retrieving an annotation therefor as a classification for the given pattern.

18. The computer program product of claim 16, wherein the taxonomy related information comprises Lowest Common Ancestor queries.

19. The computer program product of claim 16, wherein at least some of the genome sequences have different lengths with respect to each other.

20. A computer processing system for classification of genomic patterns, comprising:
   a processor, configured to
      pre-process a taxonomy tree built to be associated with a genome database to extract taxonomy related information therefrom from which a plurality of right maximal patterns are derived, the genome database comprising a plurality of genome sequences each of which being read without a fixed length requirement during a-preprocessing of the taxonomy tree;
      build a suffix tree on the genome database; and
      annotate nodes in the suffix tree, using the plurality of right maximal patterns as annotations, such that each of the plurality of right maximal patterns in the suffix tree points to a respective one of a plurality of nodes in the taxonomy tree and such that a leaf node in the taxonomy tree represents a respective sample organism, the annotations configured to function as classifications for the plurality of genome sequences, wherein the suffix tree is built and the nodes in the suffix tree are annotated as part of a pre-processing of the taxonomy tree.

* * * * *